(12) United States Patent
Pinapala Venkata et al.

(10) Patent No.: US 9,549,052 B2
(45) Date of Patent: Jan. 17, 2017

(54) SYSTEM AND METHOD FOR MANAGING ALCOHOL CONSUMPTION OF A USER USING A SMARTPHONE APPLICATION

(71) Applicant: Cyberliver Limited, Stanmore (GB)

(72) Inventors: Bharadwaj Ragavendra Prasad Pinapala Venkata, Chennai (IN); Ravi Kumar Kalkivayi Seshagiri, Westhoughton (GB)

(73) Assignee: Ciberliver Limited, Stanmore (GB)

( * ) Notice: Subject to any disclaimer, the term of this patent is extended or adjusted under 35 U.S.C. 154(b) by 380 days.

(21) Appl. No.: 14/082,393

(22) Filed: Nov. 18, 2013

(65) Prior Publication Data

US 2014/0139665 A1    May 22, 2014

(30) Foreign Application Priority Data

Nov. 19, 2012  (GB) .................................. 1220772.6

(51) Int. Cl.
| | |
|---|---|
| *G01N 33/497* | (2006.01) |
| *G08B 21/02* | (2006.01) |
| *H04M 1/21* | (2006.01) |
| *H04M 1/725* | (2006.01) |

(52) U.S. Cl.
CPC ............... *H04M 1/21* (2013.01); *G08B 21/02* (2013.01); *H04M 1/72522* (2013.01); *G01N 33/4972* (2013.01); *H04M 2250/52* (2013.01)

(58) Field of Classification Search
CPC  H04M 1/21; H04M 1/72522; H04M 2250/52; G01N 33/4972; G08B 21/02; H04N 7/182
See application file for complete search history.

(56) References Cited

U.S. PATENT DOCUMENTS

| | | | | |
|---|---|---|---|---|
| 6,017,308 A | * | 1/2000 | Fults | .................. G01N 33/4972 |
| | | | | 600/300 |
| 7,962,342 B1 | * | 6/2011 | Coughlan | ............... G10L 15/22 |
| | | | | 379/201.01 |

(Continued)

OTHER PUBLICATIONS

Nan Li and Guanling Chen, "Analysis of a location-based social network," International Conference on Computational Science and Engineering, vol. 4. IEEE, 2009.*

*Primary Examiner* — Thai Tran
*Assistant Examiner* — Christopher T Braniff
(74) *Attorney, Agent, or Firm* — The Law Office of Austin Bonderer, PC; Austin Bonderer

(57) ABSTRACT

A device for managing alcohol consumption of a user includes a camera that captures an image associated with a beverage container, a display unit, a memory unit that stores (a) a set of modules, and (b) a database, and (iv) a processor that executes (a) an alcohol content identification module, when executed by the processor, identifies (i) a type of drink in the beverage container and (ii) an alcohol content associated with the drink, (b) an alcohol consumption determination module, executed by the processor, determines an alcohol consumption by the user, (c) an alcohol consumption updating module, when executed by the processor, updates the alcohol consumption by the user in the database, and (d) an alert generation module, when executed by the processor, generates an alert when the alcohol consumption by the user is in proximity with the at least one of periodic threshold.

11 Claims, 19 Drawing Sheets

(56) References Cited

U.S. PATENT DOCUMENTS

| | | | |
|---|---|---|---|
| 2002/0047867 A1* | 4/2002 | Mault | A61B 5/1118 715/810 |
| 2006/0217932 A1* | 9/2006 | Vercnocke | G06Q 50/26 702/187 |
| 2010/0012417 A1* | 1/2010 | Walter | B60K 28/063 180/272 |
| 2010/0283601 A1* | 11/2010 | Tai | G06Q 50/24 340/539.12 |
| 2011/0063468 A1* | 3/2011 | Ahn | G06K 9/3258 348/222.1 |

* cited by examiner

| DRINK | TYPE OF DRINK 502 | ALCOHOL CONTENT 504 | QUANTITY (Pint) 506 |
|---|---|---|---|
| DRINK | CIRCLE BLUR TEXAS HEFE BEER | 4.6% | 1.0 |

FIG. 5B

| DRINK | TYPE OF DRINK 602 | ALCOHOL CONTENT 604 | QUANTITY 606 |
|---|---|---|---|
| DRINK A | CIRCLE ENVY AMBER BEER | 4.8% | 1 PINT |
| DRINK B | CIRCLE BLUR TEXAS HEFE BEER | 4.6% | 0.5 PINT (Half-empty container) |
| DRINK C | TWISTED TEA ORIGINAL FLAVOURED BEER | 5.0% | 2 PINT |

SYSTEM AND METHOD FOR MANAGING ALCOHOL CONSUMPTION OF A USER USING A SMARTPHONE APPLICATION

BACKGROUND

Technical Field

The embodiments herein generally relate to alcohol consumption management systems, and, more particularly, a system and method for obtaining information associated with alcohol consumption behavior of a user and facilitating the user in managing his/her drinking behavior.

Description of the Related Art

People consume alcohol sporadically without keeping track of their consumption. Excessive alcohol consumption leads to health problems, family problems, loss of productivity at work places, etc. Typically, there exist a number of applications which enable an individual to keep tracking their drinking habits.

AlcoDroid Alcohol Tracker, developed by Myrecek is an alcohol consumption tracker application for a mobile phone, in which an individual logs drinks which have been consumed. The EAC is plotted on a chart and it indicates when alcohol consumption by the individual reaches a legal limit for driving, or subsequently when blood alcohol content (BAC) level of the individual gets back to zero.

A blood alcohol calculator developed by Hauki, is an application for a mobile phone, in which an individual may provide quantity of one or more drinks (e.g., beer, wine, and spirits) which have been consumed. Accordingly, the application computes and displays a maximum blood alcohol level of the individual.

An alcohol calculator developed by Pawel Nadolski, is also an application for a mobile phone. An individual has to enter number of alcoholic drinks consumed by the individual and a finish time of drink. The application computes and displays blood alcohol concentration and an estimated time at which blood alcohol level will drop to an allowable limit for driving.

A blood alcohol calculator developed by CityJams is a simple calculator that provides a list of common drink types. An individual has to enter his/her weight, time spent in drinking, and types of drinks consumed. The blood alcohol calculator then calculates the blood alcohol content (BAC) level.

Drink Droid Plus BAC Calculator developed by Laby, is an application for estimating the blood alcohol content (BAC) level based on types and quantity of drinks consumed by an individual.

Another example of a blood alcohol content calculator is jAlcoMeter, developed by Tuukka Haapasalo. The application works by allowing a user to input each drink in a real-time, or later if he/she forgets. Personal information such as a gender and a weight is captured to enable the BAC level estimation, and current intoxication level is indicated. However, whilst this application gives an indication of how intoxicated a person is becoming, it is necessary for the individual to enter details of each drink consumed, which is likely to be inaccurate in various circumstances. The application does not support individuals to modify their drinking habits or fails to indicate whether their drinking habits have caused any long term problem.

KR 100286129 discloses a portable phone having a "drunkometer" function to add functions of a breathalyzer to a portable terminal. A "drunken alarm message" display on the portable phone is connected to an alcohol concentration detection sensor. A ROM connected with the message display, stores a required drunken alarm messages.

Accordingly, thus whilst portable breathalyzers exist and mobile device applications operable to enable an individual to log a number of drinks consumed exist. However, there remains a need for an alcohol management system that gives support to individuals in modify their drinking habits.

SUMMARY

In view of the foregoing, an embodiment herein provides a device for managing alcohol consumption of a user. The device includes (i) a camera that captures an image associated with a beverage container, (ii) a display unit, (iii) a memory unit that stores (a) a set of modules, and (b) a database, and (iv) a processor that executes the set of modules. The database stores one or more periodic threshold associated with alcohol consumption by the user. The set of modules includes (a) an alcohol content identification module, when executed by the processor, identifies (i) a type of drink in the beverage container and (ii) an alcohol content associated with the drink, (b) an alcohol consumption determination module when executed by the processor, determines an alcohol consumption by the user, (c) an alcohol consumption updating module when executed by the processor, updates the alcohol consumption by the user in the database, and (d) an alert generation module when executed by the processor, generates an alert when the alcohol consumption by the user is in proximity with the at least one of periodic threshold.

The alcohol content identification module may identify (i) a type of drink in the beverage container and (ii) an alcohol content associated with the drink based on (a) a shape, (b) a brand, and (c) a barcode associated with the beverage container. The alcohol consumption determination module may determine an alcohol consumption by the user based on (i) information obtained from the image comprising a drink level in the beverage container, (ii) a user input including information on alcohol consumed by the user, and (iii) a blood alcohol content (BAC) level of the user that is measured using a breathalyzer. The set of modules may further include a drink options generation module that generates drink options for the user based on information relating to images of one or more beverage containers.

The information may include (i) an alcohol content level associated with the one or more beverage containers, (ii) a drink level in the one or more beverage containers, and (iii) the at least one of periodic threshold. The set of modules may further includes (a) a location information obtaining module, when executed by the processor, obtains a location information of the user based on a social medium update relating to the user's location, and (b) a message generation module, when executed by the processor, generates a message that prompts the user to specify any alcohol consumed by the user during a time spent by the user at a location. The set of modules may further include (a) a blood alcohol content (BAC) level record module, when executed by the processor, records a BAC level associated with the user when the user utilizes a breathalyzer for measuring BAC level, and (b) an electronic diary generation module, when executed by the processor, generates an electronic diary that indicates one or more (i) blood alcohol content (BAC) level associated with the user, and (ii) alcohol consumption by the user as a function of time. The set of modules may further include a location based message generation module, when executed by the processor, (a) obtains a current location of the user, (b) alerts the user to plan a transportation support when the user's blood alcohol content (BAC) level is more than at least one periodic threshold, (c) generates a message that include one or more (i) the current location of the user, and (ii) an URL associated with a map or a map that indicates the current location of the user, and (d) communicates the message to a communication device associated with a third party who provides the transportation support.

In another aspect, a method for managing alcohol consumption of a user is provided. The method includes (i) obtaining an image associated with a beverage container, (ii) identifying (a) a type of drink in the beverage container and (b) an alcohol content associated with the drink, (iii) determining an alcohol consumption by the user, (iv) updating the alcohol consumption by the user in a database, and (v) generating an alert when the alcohol consumption by the user is in proximity with the one or more periodic threshold. The database stores the one or more periodic threshold associated with alcohol consumption by the user.

A type of drink in the beverage container may be identified. An alcohol content associated with the drink may be identified based on at least one of (a) a shape, (b) a brand, and (c) a barcode associated with the beverage container. The alcohol consumption by the user may be determined based on one or more (i) information obtained from the image comprising a drink level in the beverage container, (ii) a user input includes information on alcohol consumed by the user, and (iii) a blood alcohol content (BAC) level of the user that is measured using a breathalyzer. The method may further include generating drink options for the user based on information relating to images of a plurality of beverage containers. The information may include (i) an alcohol content level associated with the plurality of beverage containers, (ii) a drink level in the plurality of beverage containers, and (iii) the one or more periodic threshold. The method may further include (a) obtaining a location information of the user based on a social medium update relating to the user's location, and (b) generating a message that prompts the user to specify any alcohol consumed by the user during a time spent by the user at a location. The method may further include (a) recording blood alcohol content (BAC) level associated with the user when the user utilizes a breathalyzer for measuring BAC level, and (b) generating an electronic diary that indicates one or more (i) blood alcohol content (BAC) level associated with the user and (ii) alcohol consumption by the user as a function of time. The method may further include (a) obtaining a current location of the user, (b) alerting the user to plan a transportation support when the user's blood alcohol content (BAC) level is more than one or more periodic threshold, (c) generating a message that include one or more (i) the current location of the user and (ii) an URL associated with a map or a map that indicates the current location of the user, and (d) communicating the message to a communication device associated with a third party who provides the transportation support.

In yet another aspect, a server for managing drinking habits of one or more users is provided. The server includes (i) a memory unit that stores (a) a set of modules, and (b) a database, and (ii) a processor that execute the set of modules. The set of modules include (a) an alert generation module, when executed by the processor, generates an alert when an alcohol consumption by a user is in proximity with the one or more periodic threshold, (b) an message generation module, when executed by the processor, generates a message that prompts the user to check a blood alcohol content (BAC) level when: (i) a current duration exceeds the preferred duration of drinking, (ii) the user indicates a current location on a social medium along with the preferred person to drink, or (iii) a current location of the user is (a) in proximity to the preferred location for drinking or (b) in proximity to a location in which the user consumed alcohol in the past, and (c) a multimedia content generation module, when executed by the processor, generates a multimedia content relating to alcohol consumption or corresponding harmful effects when the user exceeds the one or more periodic threshold. The database stores information associated with each of the one or more users. The information include one or more (a) a periodic threshold associated with alcohol consumption by the user, (b) a preferred duration of drink, (c) a preferred location to drink, and (d) a preferred person to drink with.

The set of modules may further include a reminder generation module that (i) processes an input including a mood, a sleep or a tiredness pattern associated with (a) a blood alcohol content (BAC) level, or (b) consumption of a drink, and (ii) generates a reminder that include the mood, the sleep or the tiredness pattern when the user approaches the BAC level or selects the drink for consumption. The message generation module may (i) generate the message at a random time that prompts the user to check a BAC level, and (ii) generate an alert that is communicated to a caregiver when the user fails to check a BAC level.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 5B is a table view illustrating a type of drink, an alcohol content, and a quantity of drink in the beverage container identified using the alcohol content identification module according to one embodiment of the present disclosure.

FIG. 6B is a table view illustrating a type of drink, an alcohol content, and a quantity of drink in the beverage containers identified using the alcohol content identification module according to one embodiment of the present disclosure.

DETAILED DESCRIPTION OF PREFERRED EMBODIMENTS

Figure 1:
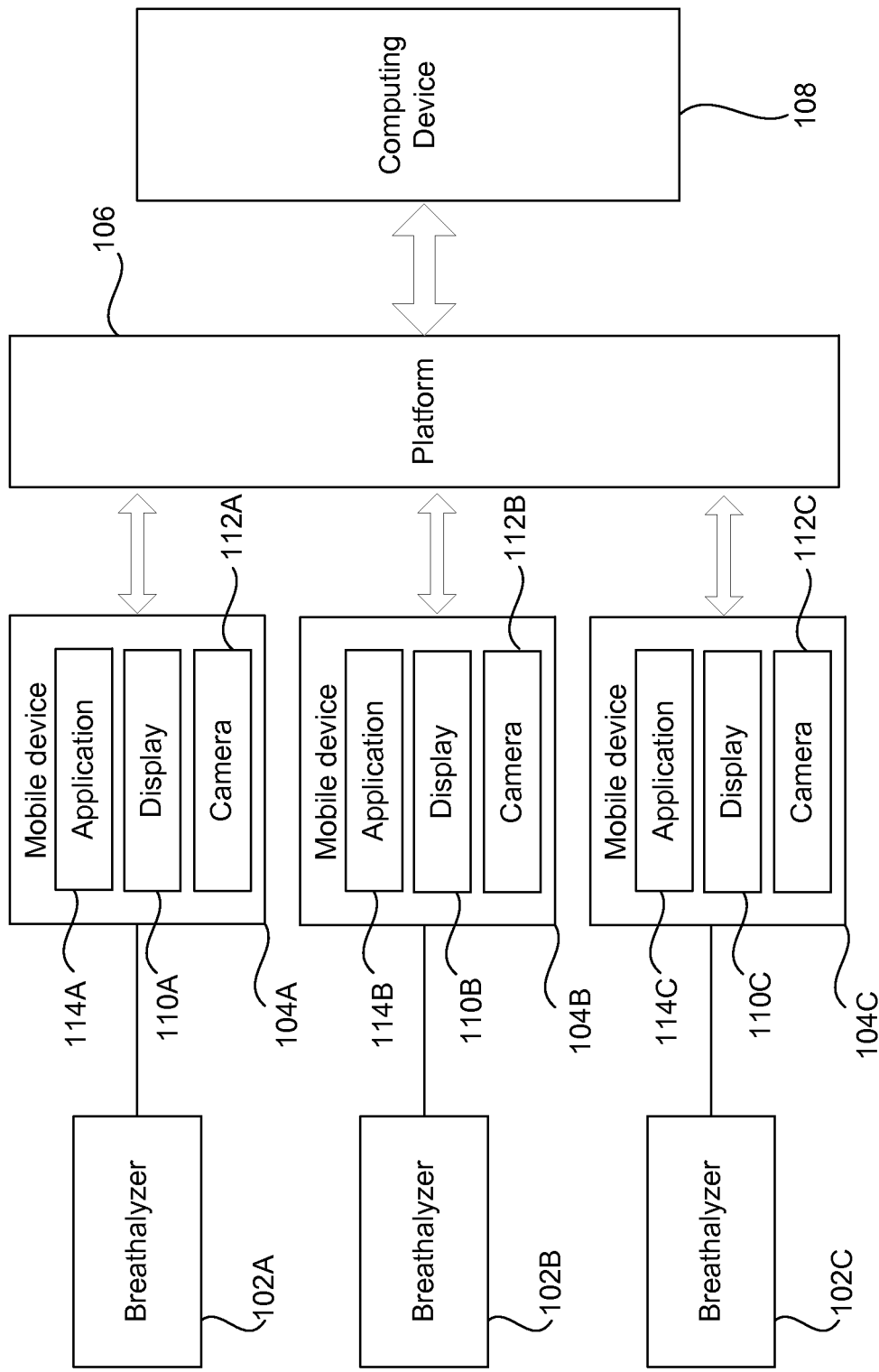
FIG. 1 illustrates a system view of an alcohol management system according to one embodiment of the present disclosure.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for an alcohol management system that gives support to individuals in modify their drinking habits. The embodiments herein achieve this by providing an alcohol management system that includes one or more mobile devices communicating information associated with alcohol consumption of users to a platform through alcohol management system application. Referring now to the drawings, and more particularly to FIGS. 1 through 15, where similar reference characters denote corresponding features consistently throughout the figures, there are shown preferred embodiments.

FIG. 1 illustrates a system view of an alcohol management system 100 according to one embodiment of the present disclosure. The alcohol management system 100 includes one or more breathalyzers 102 A-C, one or more mobile devices 104 A-C, a platform 106, a computing device 108, and users (not shown in the FIG. 1) of the alcohol management system 100. A breathalyzer 102A measures a blood alcohol content (BAC) level associated with a first user. The BAC level is communicated to the platform 106 using an alcohol management system application at the mobile device 104A. Similarly, a breathalyzer 104B and 104C measures a blood alcohol content (BAC) level of a second user and a third user respectively, and it is communicated to the platform 106. Each of the mobile devices 104A-C is in communication with the platform 106 under a control of the computing device 108. Further, each breathalyzer 102A-C is powered by the respective mobile devices 104A-C.

In one embodiment, the mobile devices 104A-C are smartphones, and each phone includes usual smartphone telephone functions, such as a keyboard to enable a user to interact with the phone and usual telecommunication functions. However, to provide clarity, only the display 110A-C on each phone is illustrated, together with the phone camera 112A-C. In accordance with the alcohol management system 100, each mobile device 104A-C includes an alcohol management system application 114A-C, as will be described in more detail hereafter. Using a camera of a mobile device, a user captures an image of a beverage container. The alcohol management system application 114A-C of the mobile device identifies a type of drink in the beverage container, an alcohol content of the drink in the beverage container, and alcohol consumption by the user based on information obtained from the image. The platform 106 provides each user with personal information based on an analysis of their BAC data and other data which is received from the users via their respective mobile device.

Figure 2:
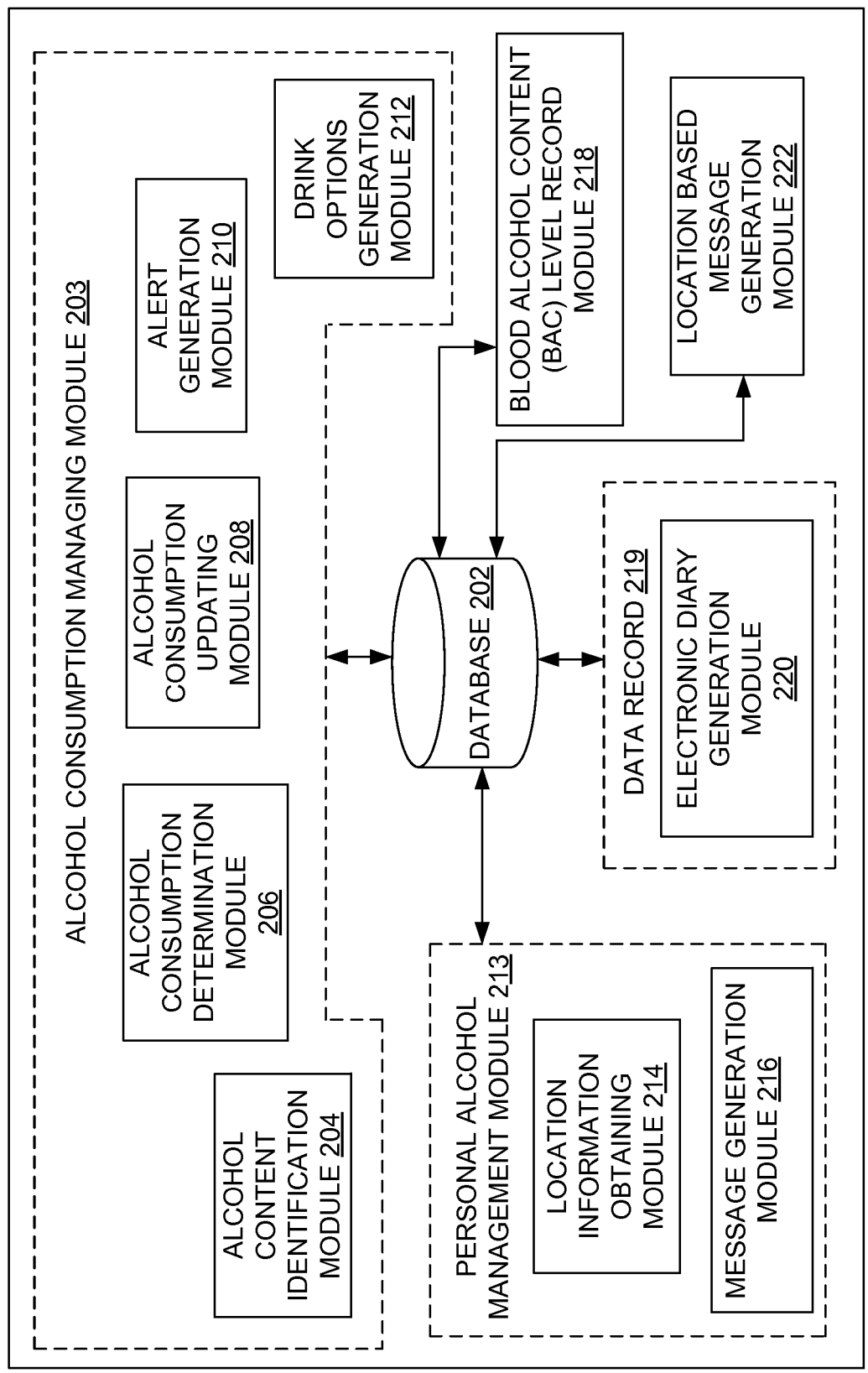
FIG. 2 illustrates an exploded view of an alcohol management system application of a mobile device according to one embodiment of the present disclosure.

With reference to FIG. 1, FIG. 2 illustrates an exploded view of the alcohol management system application 114A-C of a mobile device according to one embodiment of the present disclosure. The exploded view includes a database 202, an alcohol consumption managing module 203, a personal alcohol management module 213, a blood alcohol content (BAC) level record module 218, a data record module 219, and a location based message generation module 222. The database 202 stores at least one periodic threshold associated with alcohol consumption by one or more users. The periodic threshold indicates a user a maximum quantity of alcohol for his/her consumption in a specific period (e.g., a day, a week, and/or a month). Examples of the periodic threshold include a daily threshold that indicates a user a maximum quantity of alcohol for his/her consumption in a day, a weekly threshold indicates a user a maximum quantity of alcohol for his/her consumption in a week, and a monthly threshold indicates a user a maximum quantity of alcohol for his/her consumption in a month. In one embodiment, a user sets a periodic threshold. In another embodiment, the alcohol management system application 114A-C sets or recommends the periodic threshold automatically based on a blood alcohol content (BAC) level of the user.

The alcohol consumption managing module 203 includes an alcohol content identification module 204, an alcohol consumption determination module 206, an alcohol consumption updating module 208, an alert generation module 210, and a drinks option generation module 212. When a user captures an image of a beverage container using a camera of a mobile device, the alcohol content identification module 204 identifies (i) a type of drink in a beverage container and (ii) an alcohol content associated with the drink based on at least one of (a) shape, (b) a brand, and (c) a barcode associated with the beverage container. In one embodiment, the alcohol content identification module 204 interprets the shape and/or the brand of the beverage container (e.g., a glass container) using an edge detection technology which is applied on the image. In one embodiment, when a user scans the bar code on the beverage container (e.g., a packaged beverage container), the alcohol content identification module 204 interprets identity of the drink using a bar code reader.

The alcohol consumption determination module 206 determines an alcohol consumption by a user based on at least one of (i) information obtained from an image comprising a drink level in a beverage container, (ii) a user input including information on alcohol consumed by the user, and (iii) a blood alcohol content (BAC) level of the user that is measured using a breathalyzer. The alcohol consumption updating module 208 updates the alcohol consumption by the user in the database 202. The alert generation module 210 generates an alert when the alcohol consumption by the user is in proximity with at least one periodic threshold. For example, a daily threshold associated with alcohol consumption of a user is 2 units. When an alcohol consumed by the user for a day approaches (e.g., 1.8 units), an alert is generated to indicate the user on possible exceeding of the daily threshold.

When a user captures images associated with beverage containers using a camera of a mobile device, the drink options generation module 212 generates drink options for the user based on information relating to images of beverage containers. The information includes (i) an alcohol content level associated with the beverage containers, (ii) a drink level in the beverage containers, and (iii) the at least one of periodic threshold.

The personal alcohol management module 213 includes a location information obtaining module 214 and a message generation module 216. The location based information module 214 obtains location information of a user, where the user may have consumed alcohol based on a social medium update relating to the user's location. The message generation module 216 generates a message that prompts the user to specify any alcohol consumed by the user during a time spent by the user at a location. This information is stored in the data record 219, and a text message is displayed at a display unit of a mobile device to nudge the user to remind them to self-monitor their alcohol consumption.

The blood alcohol content (BAC) level record module 218 records a BAC level of a user every time the user utilizes a breathalyzer for measuring the BAC level. The electronic diary generation module 220 generates an electronic diary that indicates at least one of (i) blood alcohol content level and (ii) alcohol consumption by the user which are determined at various duration as a function of time.

The location based message generation module 222 generates a message to integrate with a transportation support provider in an emergency (e.g., when alcohol consumed by a user exceeds a periodic threshold). In one embodiment, the location based message generation module 222 generates an alert that prompts the user to plan or contact an emergency contact or order a transportation support (e.g., by contacting a transportation facility center or transportation service provider such as taxi owners) when the user's BAC level is more than at least one periodic threshold. The location based message generation module 222 obtains a current location of the user (e.g., using GPS or GPRS function on the user's mobile device). The location based message generation module 222 then generates a message that includes at least one of (i) the current location of the user and (ii) an URL associated with a map or a map that indicates the current location of the user, and communicates the message to a communication device associated with a third party who provides a transportation support. It will be appreciated that the alcohol management system application 114A-C can also be installed on the platform 106 instead in the mobile devices 104A-C.

Figure 3:
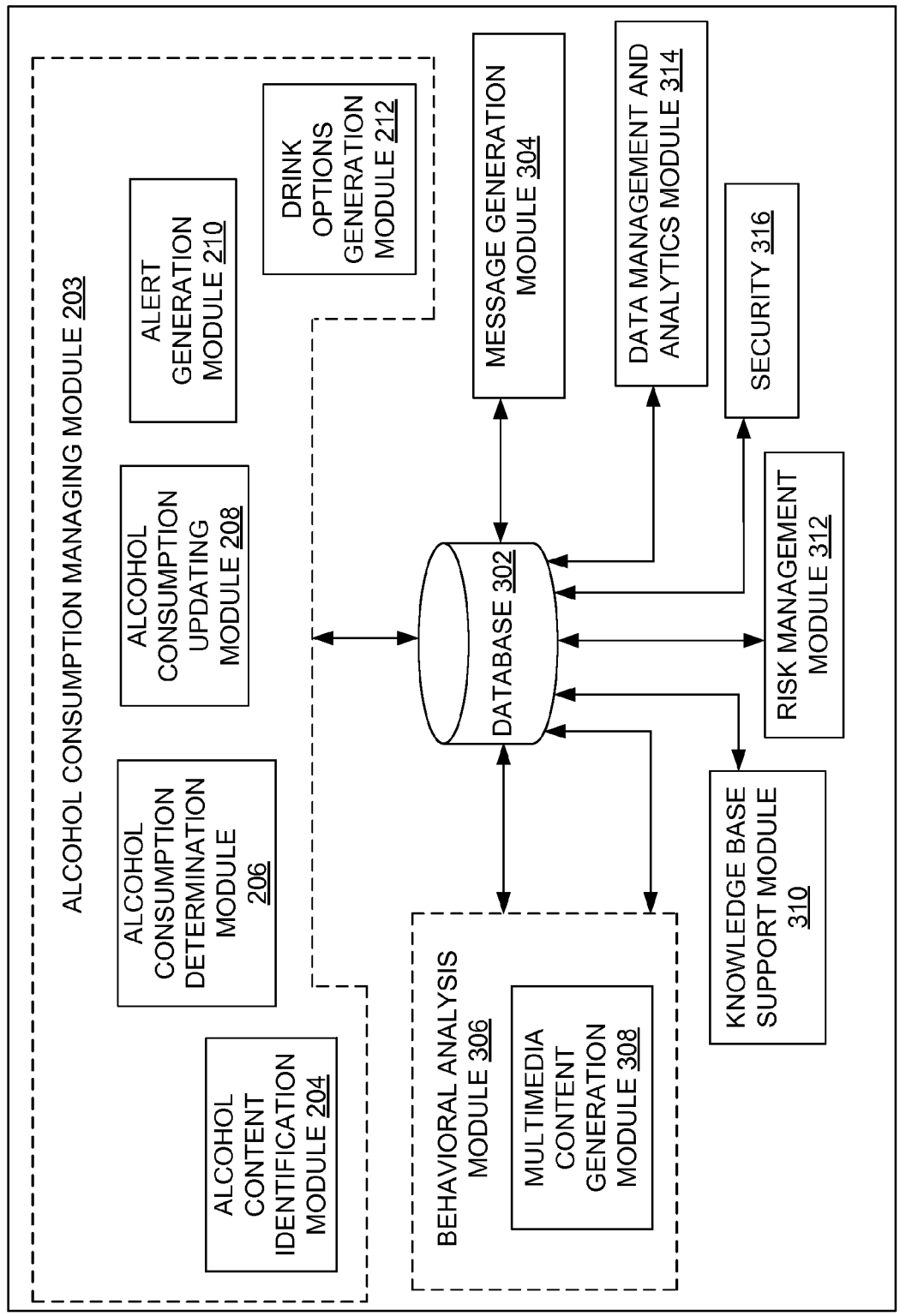
FIG. 3 illustrates an exploded view of an alcohol management platform application of the platform of FIG. 1 according to one embodiment of the present disclosure.

FIG. 3 illustrates an exploded view of an alcohol management platform application 302 of the platform 106 of FIG. 1 according to one embodiment of the present disclosure. The alcohol management platform application 302 of the platform 106 includes a database 302, the alcohol consumption managing module 203, a message generation module 304, a behavioral analysis module 306, a knowledge base support module 310, a risk management module 312, and a data management and analytics module 314. The database 302 stores, but not limited to, a) a periodic threshold associated with alcohol consumption by various users, and data such as (b) a preferred duration of drink, (c) a preferred location to drink, and (d) a preferred person to drink associated with various users.

As described above, the alcohol consumption managing module 203 includes the alcohol content identification module 204, the alcohol consumption determination module 206, the alcohol consumption updating module 208, the alert generating module 210 and the drinks option generation module 212. A user captures an image of a beverage container using a camera of a mobile device. The image is communicated to the platform 106. The alcohol consumption identification module at the platform 106 identifies (i) a type of drink in a beverage container and (ii) alcohol content associated with the drink based on at least one of (a) shape, (b) a brand, and (c) a barcode associated with the beverage container as described above. Similarly, the alcohol consumption determination module 206 determines alcohol consumption by a user, and the alcohol consumption updating module 208 updates the alcohol consumption by the user in the database 302 as described in FIG. 2. The alert generation module 210 at the platform 106 generates an alert when the alcohol consumption by the user is in proximity with at least one periodic threshold (e.g., less than or equal to the at least one periodic threshold). The platform 106 stores and process information associated with alcohol consumption by various users.

In one embodiment, the message generation module 304 generates a message that prompts a user to check a BAC level when a current duration exceeds the preferred duration of drinking. For example, the platform 106 stores information associated with alcohol consumption by a user includes a preferred duration of drink as Nov. 20, 2013 at 5 PM. The message generation module 304 generates a message that prompts the user to check a BAC level when a current time (e.g., 05.01 PM) exceeds the preferred duration of drinking (e.g., 5 PM). In one embodiment, the message is generated at regular intervals of time (e.g., for every 30 minutes after the preferred duration of drinking). In another embodiment, the message generation module 304 generates a message that prompts a user to check a BAC level when the user indicates a current location on a social medium along with the preferred person to drink. For example, the platform 106 stores information that includes a preferred person to drink with is John Doe, which is provided by the user. And when the user updates his/her current location on a social medium that indicates the user's presence with John Doe, a message is generated that prompts the user to check a BAC level.

In further embodiment, the message generation module 304 generates a message that prompts a user to check a BAC level when a current location of the user is (a) in proximity to the preferred location for drinking or (b) in proximity to a location in which the user consumed alcohol in the past. For example, the platform 106 stores information includes a preferred location for drinking associated with the user is "ABC pub". When a current location of the user is in proximity (e.g., 2 kms) to the "ABC pub", a message is generated that prompts the user to check his/her BAC level. In one embodiment, the message generation module 304 generates a message at a random time that prompts a user to check a BAC level. When the user fails to check his/her BAC level, an alert is generated and communicated to a caregiver (e.g., a clinician, a rehabilitation coordinator, an individual, or a personnel, etc). When the user checks his/her BAC level, the alcohol management platform application 302 may enable the user to capture his/her picture (e.g., a photograph of the user).

The behavioral analysis module 306 analyses data collected from various users and is able to engage with the users, by sending them appropriate messages (e.g., motivational messages). The behavioral analysis module 306 further includes a multimedia content generation module 308 that generates a multimedia content relating to alcohol consumption or corresponding harmful effects when a user exceeds a periodic threshold. For example, when the user exceeds a periodic threshold, an image that indicates a user how he/she looks in the future (e.g., after 10 years) by continuing current alcohol consumption level. In another example, the multimedia content generation module 308 generates a multimedia content that indicates harmful effects of alcohol consumption when the user exceeds the periodic threshold.

The knowledge base support module 310 also provides facts, news and updates via RSS feeds to users in able to encourage them keep their awareness of alcohol consumption. The risk management module 312 analysis data received from the mobile devices and computes if the users are at risk. If any potential risks are found, the users are sent relevant warning messages to their mobile device via a messaging unit. The data management and analytics module 314 manages incoming data and provides an analysis of trends in the data. Appropriate security measure 316 is built into the platform 106, to avoid infiltration from unauthorized parties, for example via the use of passwords on a mobile device.

The alcohol management platform application 302 further includes a reminder generation module (not shown in the FIG. 3). The reminder generation module processes an input including a state of mind or a state of feeling (e.g., an emotion state such as a mood, sleep, and/a tiredness) associated with (a) a BAC level, or (b) consumption of a drink. The reminder generation module generates a reminder that includes the mood, the sleep, and/or the tiredness pattern when the user approaches the BAC level or selects the drink for consumption in the future. For example, the reminder generation module processes an input from a user including a mood pattern as bad, a sleep pattern is not good, and a tiredness pattern as very tired which are all associated with consumption of a drink 'XYZ' or a BAC level. When the user selects the same drink 'XYZ' or approaches the BAC level in the future, a reminder is generated that includes the mood, the sleep, and/or the tiredness pattern associated with the consumption of the drink 'XYZ' in the past or the BAC level, and is displayed to the user.

Figure 4:
FIG. 4 illustrates a user interface view associated with logging into an alcohol management system application of a mobile device of FIG. 1 according to one embodiment of the present disclosure.

FIG. 4 illustrates a user interface view associated with logging into an alcohol management system application 114A-C of the mobile devices 104A-C of FIG. 1 according to one embodiment of the present disclosure. The user interface view includes a username field, a password field, a login field, and a sign up field. A user login into the alcohol management system application, and obtains, records, monitors, and manages information related to his/her drinking habits.

Figure 5A:
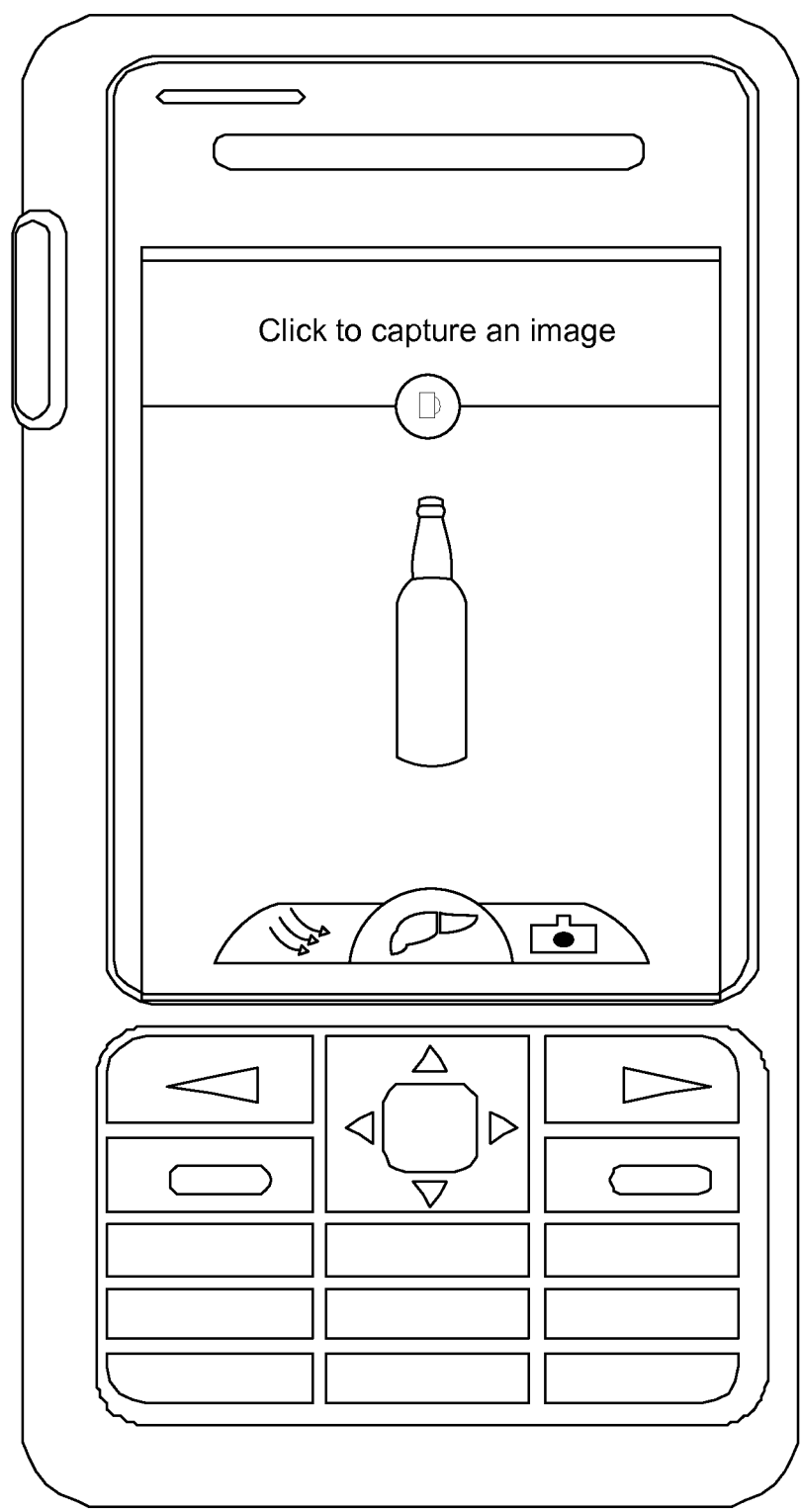
FIG. 5A illustrates a user interface view of a mobile device that displays an image of a beverage container captured using a camera of the mobile device by a user according to one embodiment of the present disclosure.

FIG. 5A illustrates a user interface view of a mobile device that displays an image of a beverage container captured using a camera of the mobile device by a user according to one embodiment of the present disclosure. With reference to the FIG. 5A, FIG. 5B is a table view illustrating a type of drink 502, an alcohol content 504, and a quantity 506 of drink in the beverage container identified using the alcohol content identification module 204 according to one embodiment of the present disclosure. The alcohol content identification module process the image of the beverage container, and obtains the type of drink 502, the alcohol content 504, and the quantity 506 based on at least one of (a) a shape, (b) a brand, and (c) a barcode associated with the beverage container.

In one embodiment, the alcohol consumption determination module 206 determines alcohol consumption by the user based on the drink level (e.g., 1 pint) in the beverage container. In another embodiment, the alcohol consumption determination module 206 processes an input from the user including information on alcohol consumption (e.g., 0.7 pint of Circle Blur Texas Hefe Beer) by the user. In further embodiment, the alcohol consumption determination module 206 determines alcohol consumption by the user based on a BAC level of the user that is measured using a breathalyzer. The alert generation module 210 generates an alert when the alcohol consumption by the user (e.g., 0.8 pint) is in proximity with at least one periodic threshold (e.g., 1 pint for a week).

Figure 6A:
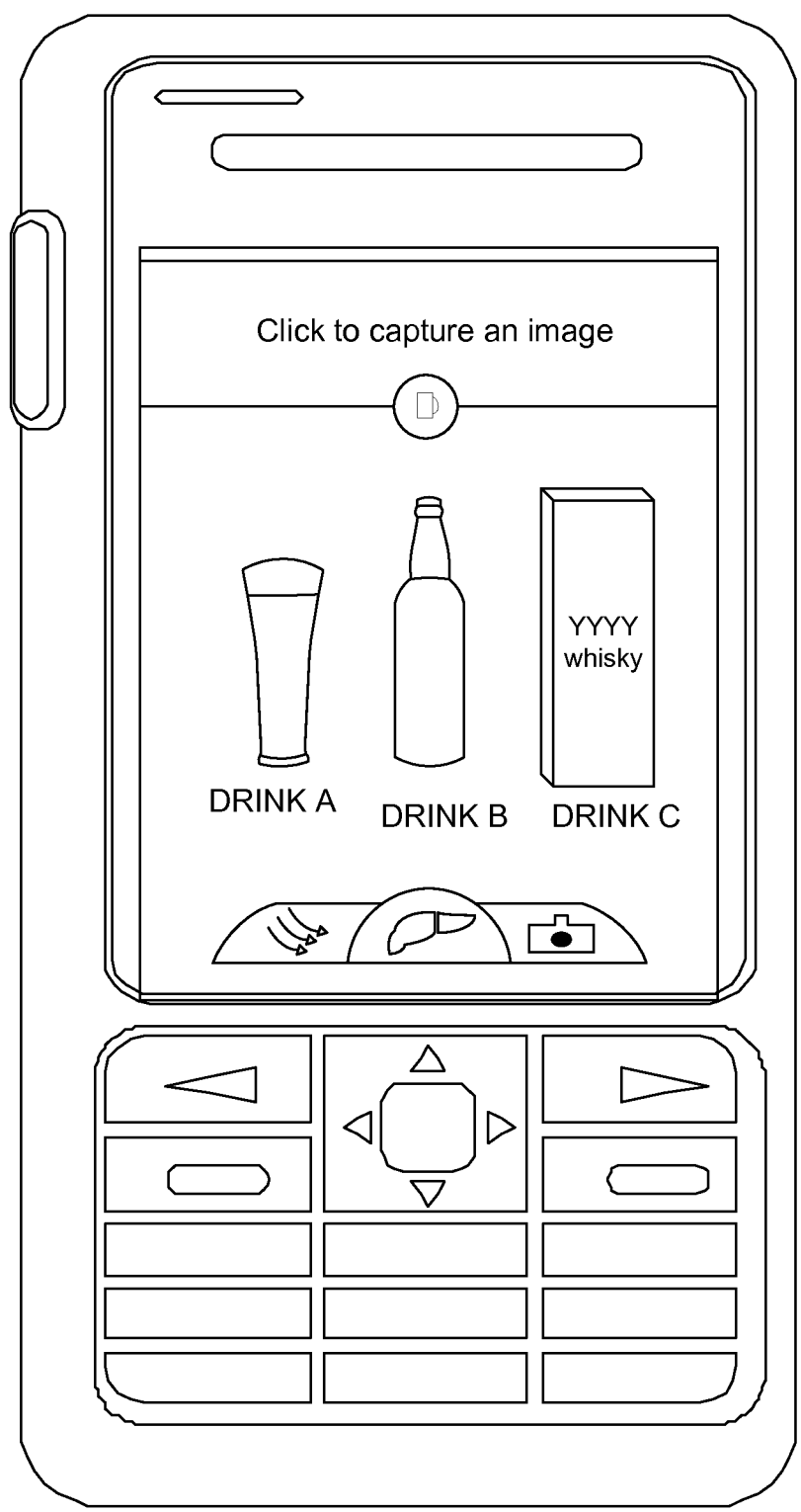
FIG. 6A illustrates a user interface view of a mobile device that displays images of beverage containers captured using a camera of the mobile device by a user according to one embodiment of the present disclosure.

FIG. 6A illustrates a user interface view of a mobile device that displays images of beverage containers captured using a camera of the mobile device by a user according to one embodiment of the present disclosure. With reference to the FIG. 6A, FIG. 6B is a table view illustrating a type of drink 602, an alcohol content 604, and a quantity 606 of drink in the beverage containers identified using the alcohol content identification module 204 according to one embodiment of the present disclosure. The drinks options generation module 212 generates drink options for the user based on information obtained from images of the beverage containers.

For example, a daily threshold associated with alcohol consumption by the user is 1.2 pints. With the information obtained from the images of the beverage containers include the type of drink 602, the alcohol content 604, and the quantity 606, the drinks option generation module 212 generates options include drink 'A' and drink 'B' for user consumption. The drinks option generation module 212 removes drink 'C' from the options, since consumption of drink 'C' cause exceeding the daily threshold of the user. The options may be prioritized and displayed to the user based on user's favorite drink, alcohol content level, periodic threshold, etc.

Figure 7:
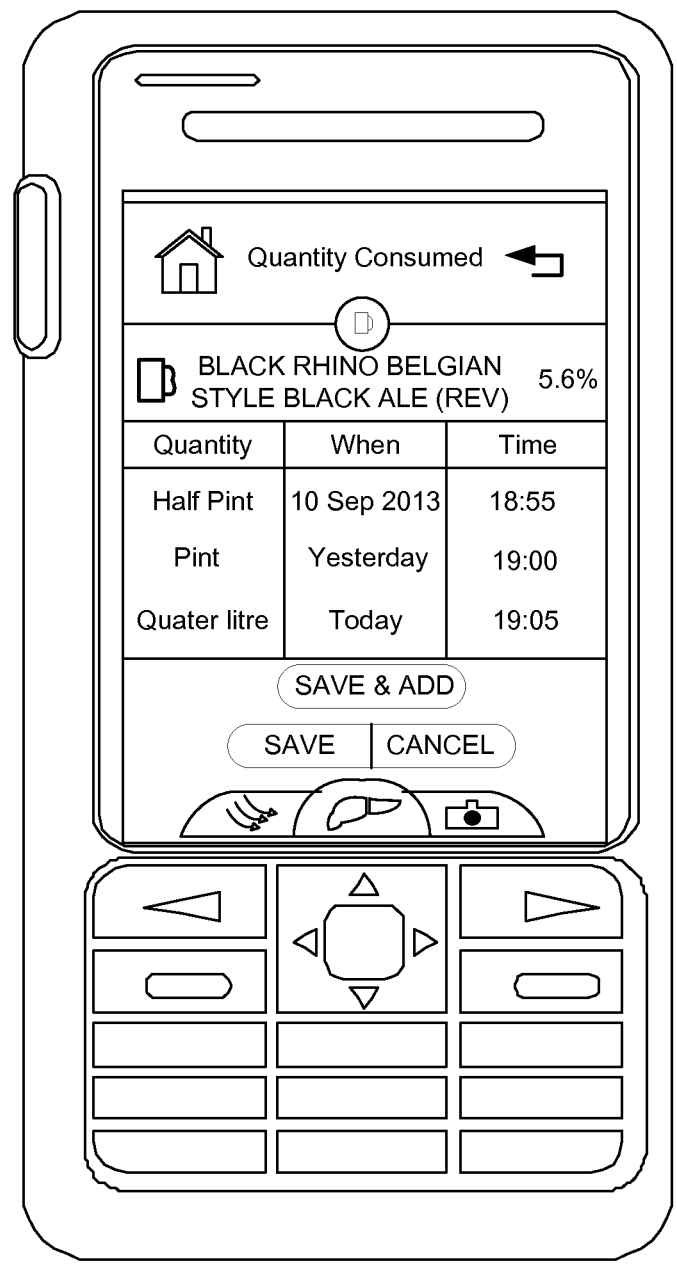
FIG. 7 illustrates a user interface view of an alcohol management system application of FIG. 1 that allows a user to input data on alcohol consumption according to one embodiment of the present disclosure.

FIG. 7 illustrates a user interface view of an alcohol management system application 114A-C of FIG. 1 that allows a user to input data on alcohol consumption according to one embodiment of the present disclosure. The alcohol management system application 114A-C processes an input (e.g., information on alcohol consumption) from the user, and obtains a quantity of alcohol consumed by the user and duration (e.g., a date and time) associated with the consumption. Similarly, the alcohol management system application 114A-C allows the user to add information on alcohol consumption at various occasions. Using the alcohol management system application 114A-C, the user can edit (e.g., editing a quantity from a half pint to a quarter pint or cancelling the event) previously inputted information on alcohol consumption.

Figure 8A:
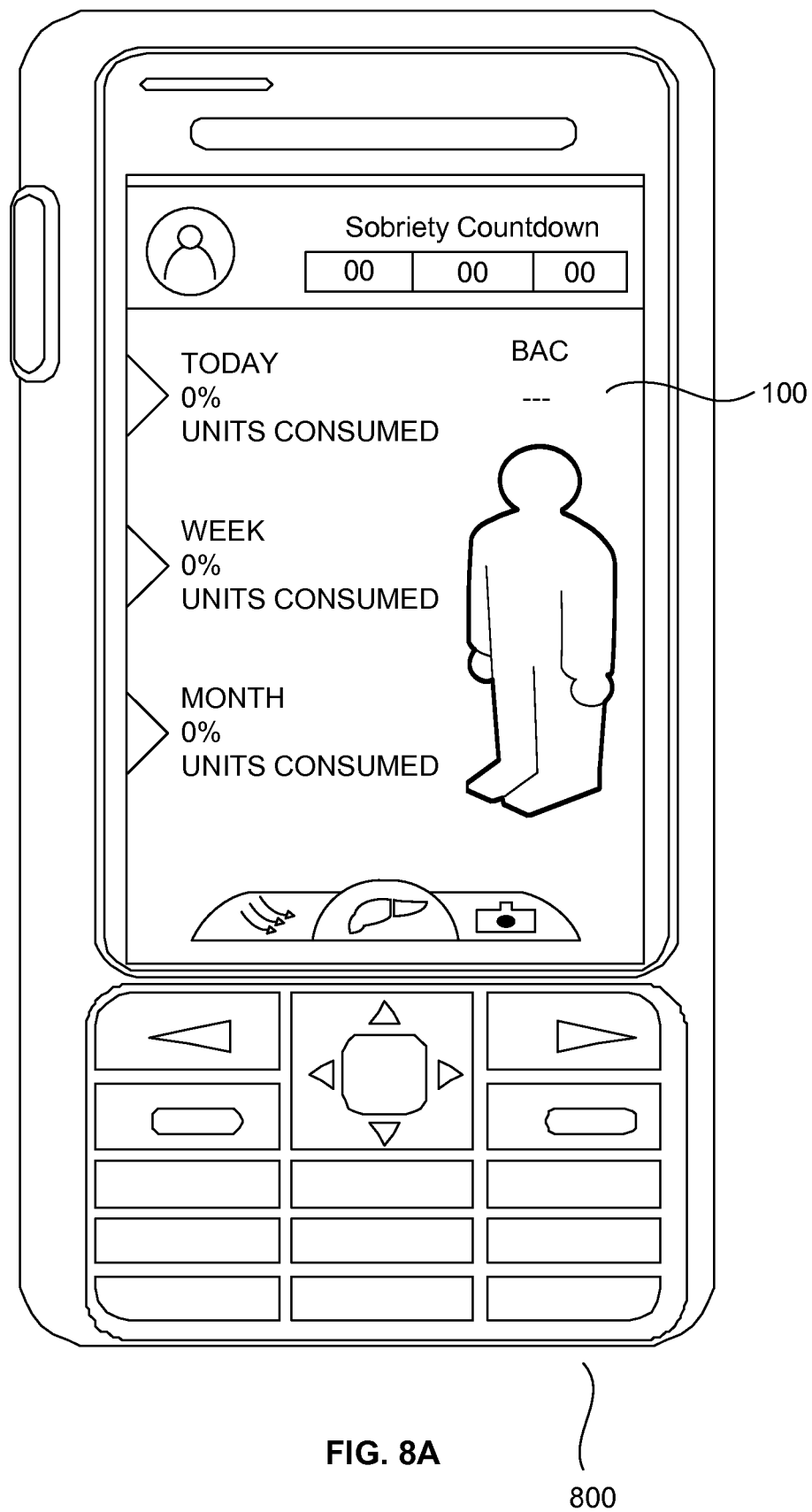
FIG. 8A illustrates a user interface view of an alcohol management system application of FIG. 1 that displays a sobriety countdown and units of alcohol consumed by a user according to one embodiment of the present disclosure.

FIG. 8A illustrates a user interface view 800 of an alcohol management system application 114A-C of FIG. 1 that displays a sobriety countdown and units of alcohol consumed by a user according to one embodiment of the present disclosure. The alcohol management system application 114A-C records units of alcohol consumed by a user over a duration, and it is displayed at the user interface. For example, the alcohol management system application 114A-C displays information on units of alcohol consumed by a user today (e.g., 0%), over a week (e.g., 2%), and over a month (e.g., 5%) in the user interface. In one embodiment, alcohol consumed by the user over a duration is determined using the alcohol consumption determination module 206. In one embodiment, the sobriety countdown is calculated based on data related to units of alcohol consumed by the user, which is recorded in the data record module 219. The user interface view 800 may also include options to trigger an emergency contact alert, integrate with a breathalyzer, an application settings page and a drink image recognition page.

Figure 8B:
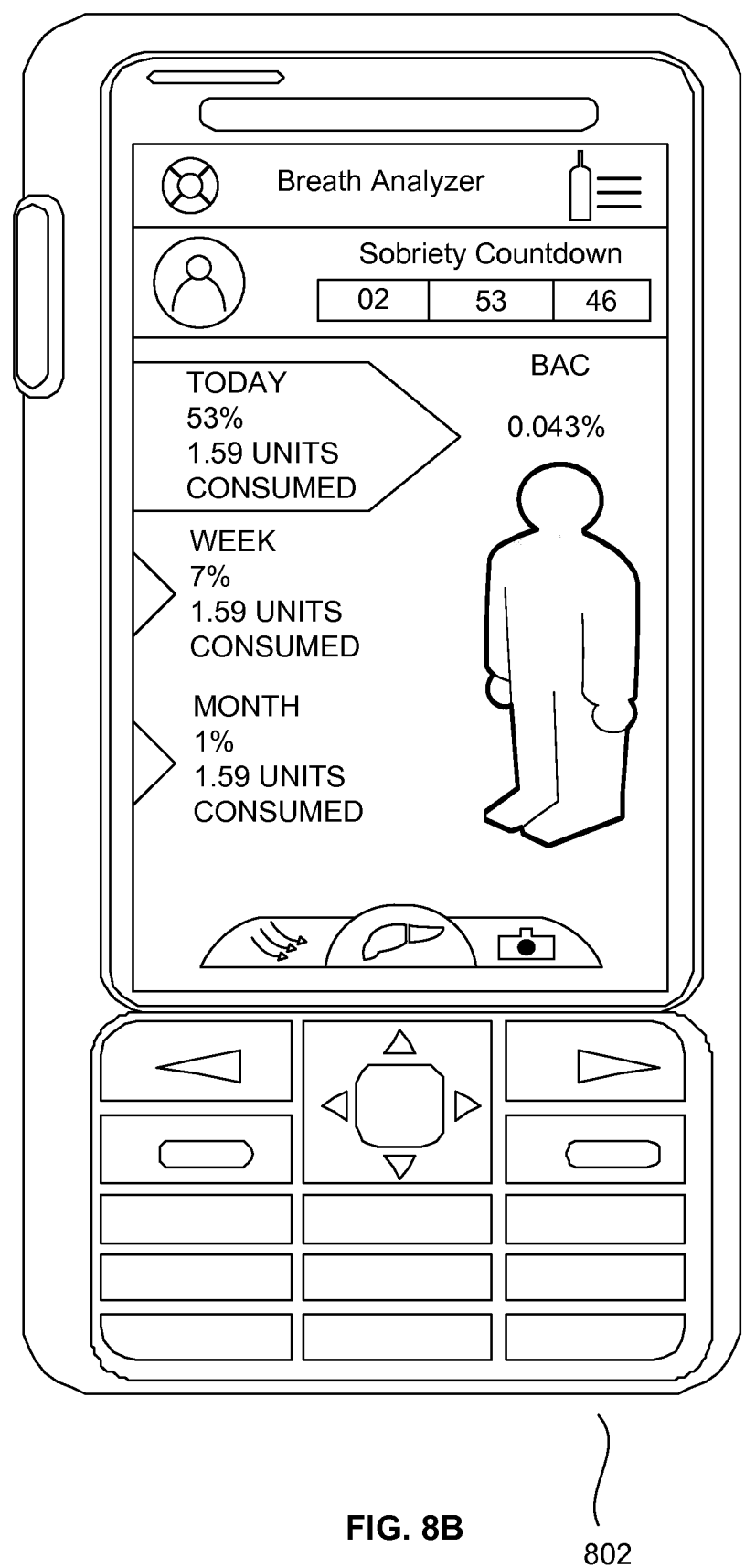
FIG. 8B illustrates a user interface view of an alcohol management system application of FIG. 1 that displays a previously recorded BAC level associated with a user and units of alcohol consumed by the user according to an embodiment herein.
Figure 9:
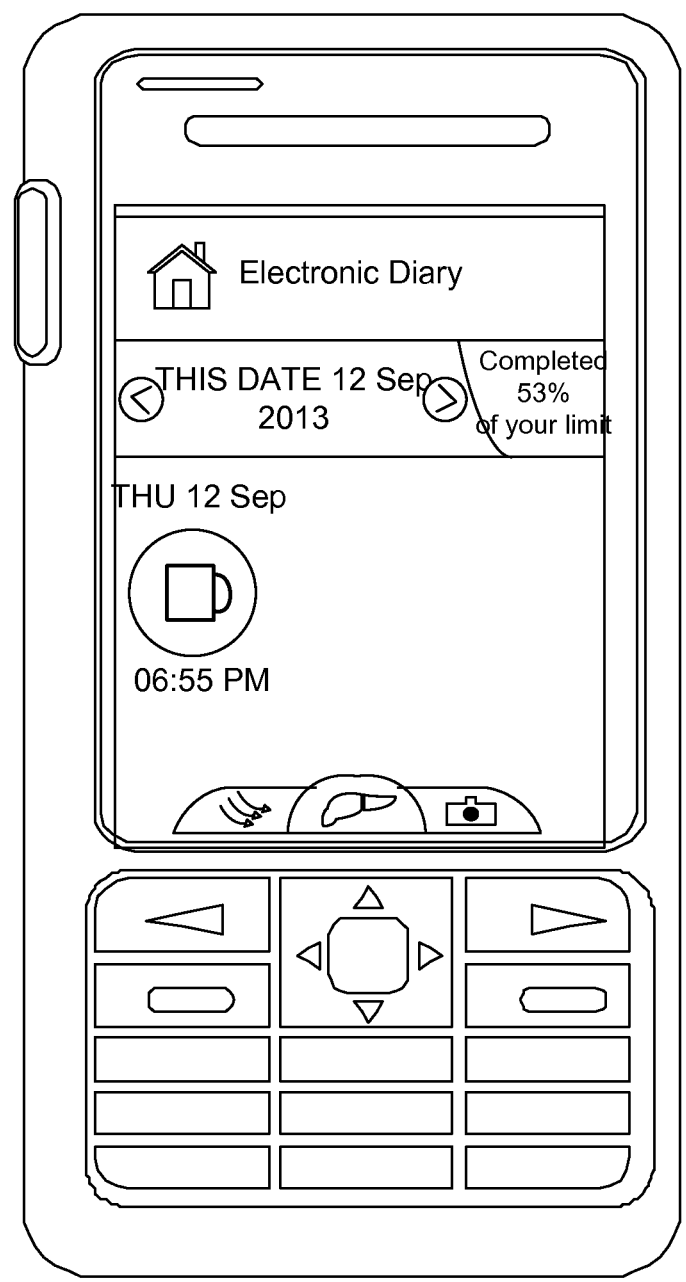
FIG. 9 illustrates a user interface view of the electronic diary generation module of FIG. 2 according to one embodiment of the present disclosure.
Figure 10:
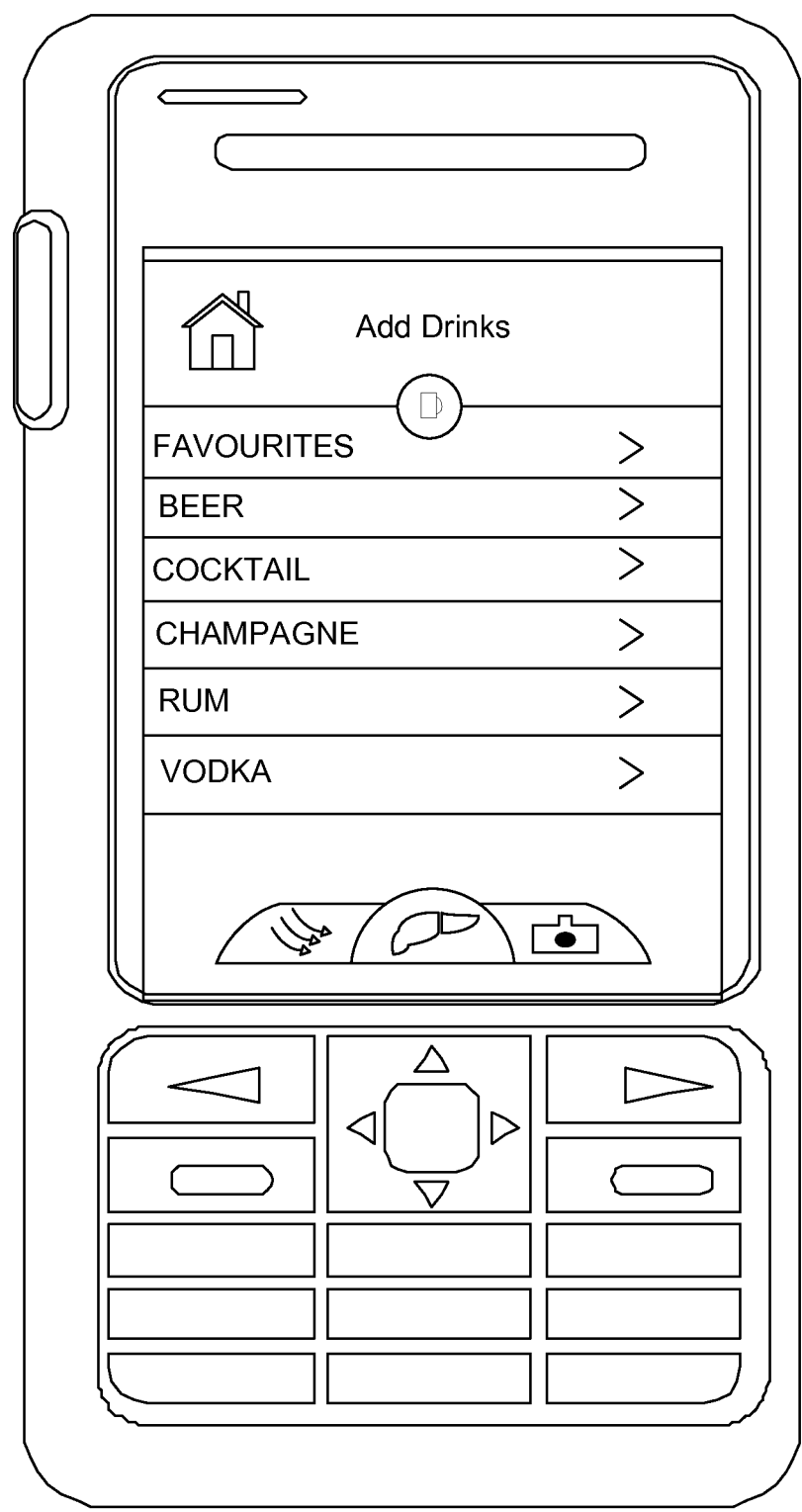
FIG. 10 illustrates a user interface view of an alcohol management system application of FIG. 1 that allows a user to select one or more drinks from the data record module of FIG. 2 according to one embodiment of the present disclosure.
Figure 11:
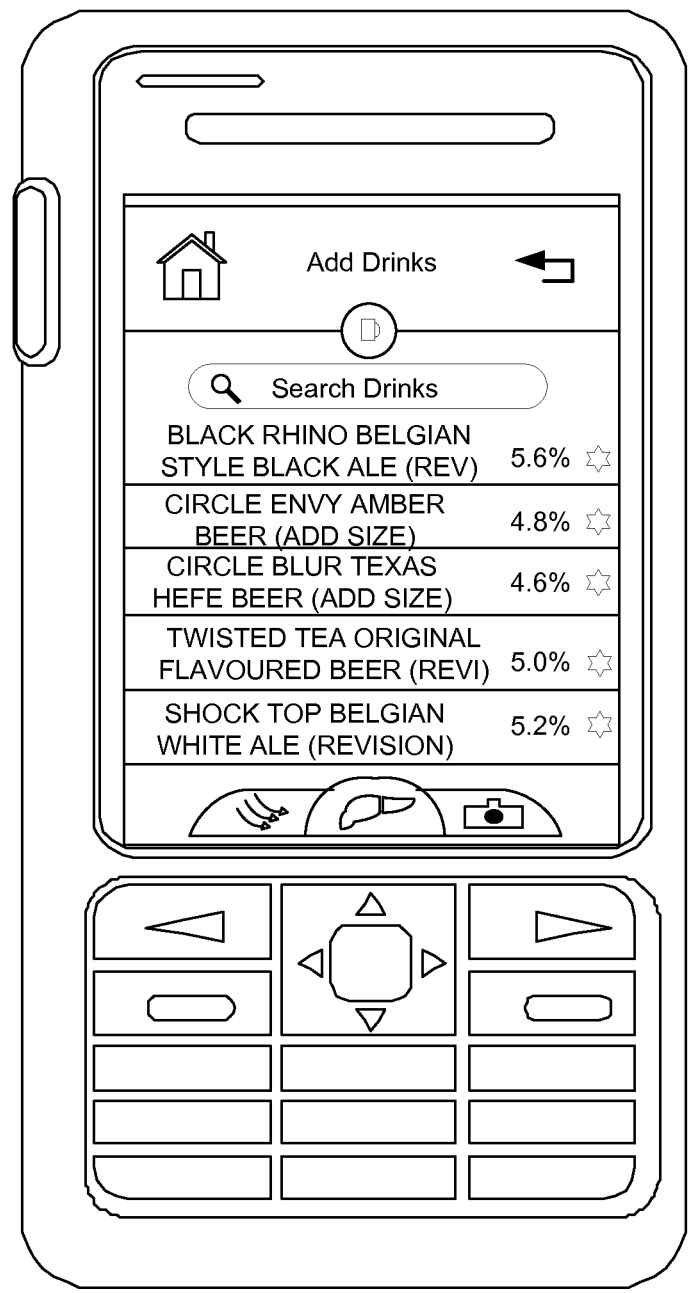
FIG. 11 illustrates a user interface view of an alcohol management system application that displays a list of generated drinks that matches a search query according to one embodiment of the present disclosure.

With reference to FIG. 8A, FIG. 8B illustrates a user interface view 802 of an alcohol management system application 114A-C of FIG. 1 that displays a previously recorded BAC level and units of alcohol consumed by the user according to an embodiment herein. Displaying units of alcohol consumed by the user helps them to manage their consumption level.

With reference to FIGS. 1 through 8B, FIG. 9 illustrates a user interface view of the electronic diary generation module 220 of FIG. 2 according to one embodiment of the present disclosure. The data record module 219 stores (i) blood alcohol content (BAC) level associated with a user and (ii) alcohol consumption by the user that are captured over a period of time. The electronic diary generation module 220 processes an input from the user including a selection of a date range, and generates an electronic diary that indicates BAC level and/or alcohol consumed by the user for the date range as a function of time. The electronic diary helps users to maintain a visual record on a phone display of units of alcohol consumed. Inbuilt mechanisms are provided to warn users when they have reached a daily, weekly or monthly threshold. Other information is provided to users with measurement tools such as CAGE and AUDIT-C questionnaires to identify users that may have alcohol dependent syndrome. CAGE and AUDIT-C are tests which help an individual assess effects of alcohol consumption on them. Details of these tests are found in for example http://en.wikipedia.org/wiki/CAGE_questionnaire, and http://en.wikipedia.org/wiki/Alcohol_Use_disorders_Identification_Test#cite_note-1. Links may be provided to interface directly to RSS feeds and websites which provide direct advice on alcohol dependence.

With reference to FIGS. 1 through 9, FIG. 10 illustrates a user interface view 1000 of an alcohol management system application 114A-C of FIG. 1 that allows a user to select one or more drinks from the data record module 219 of FIG. 2 according to one embodiment of the present disclosure. Using the alcohol management system application 114A-C, the user adds one or more favorite drinks to the data record module 219. The alcohol management system application 114A-C further allows the user to search a drink by a name, and/or a predefined drink category filter search. The interface view 1000 displays a list of drinks that are marked as a favorite drink by the user. The list of drinks may help the user in searching a drink in a short period of time.

With reference to FIGS. 1 through 10, FIG. 11 illustrates a user interface view of an alcohol management system application 114A-C that displays a list of generated drinks that matches a search query according to one embodiment of the present disclosure. Every drink in the list includes an option to be marked as a favorite drink, and automatically adds to favorites in the data record module 219. The user may also mark a drink as a non-favorite drink, and removes the drink from a list of favorite drink.

Figure 12A:
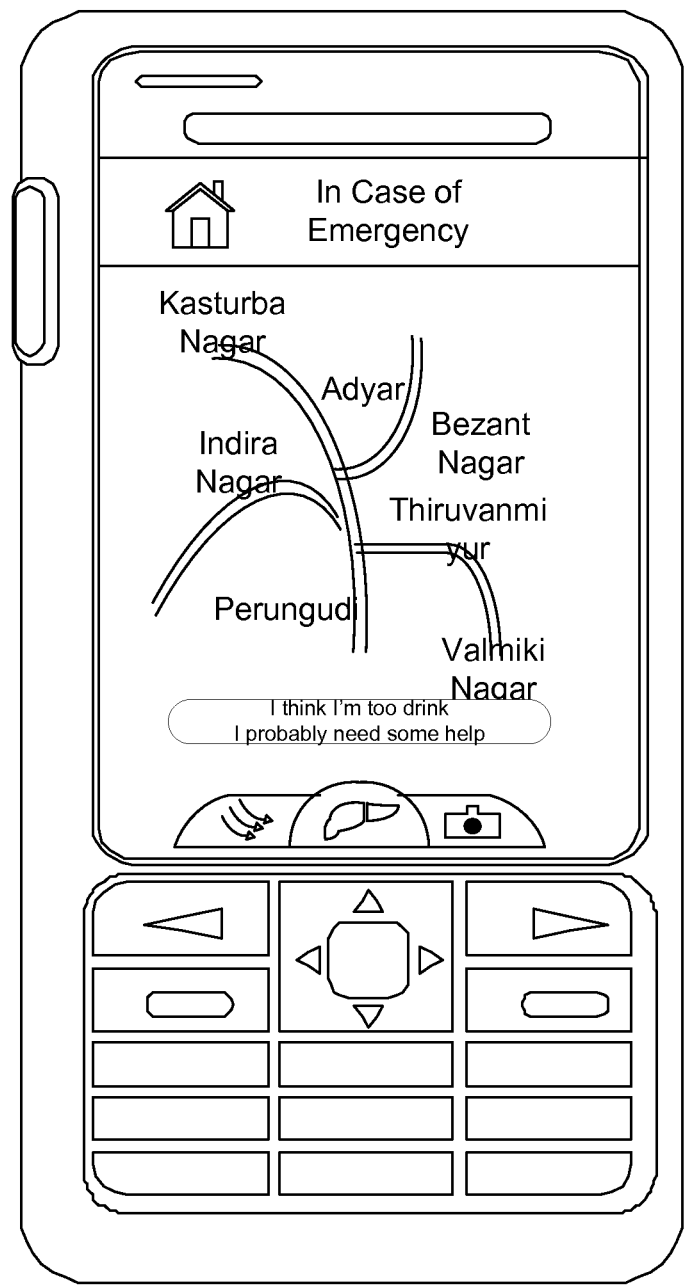
FIG. 12A illustrates a user interface view of a message that includes a map indicating a current location of a user, which is communicated to a communication device associated with a third party who provides a transportation support according to one embodiment of the present disclosure.
Figure 12B:
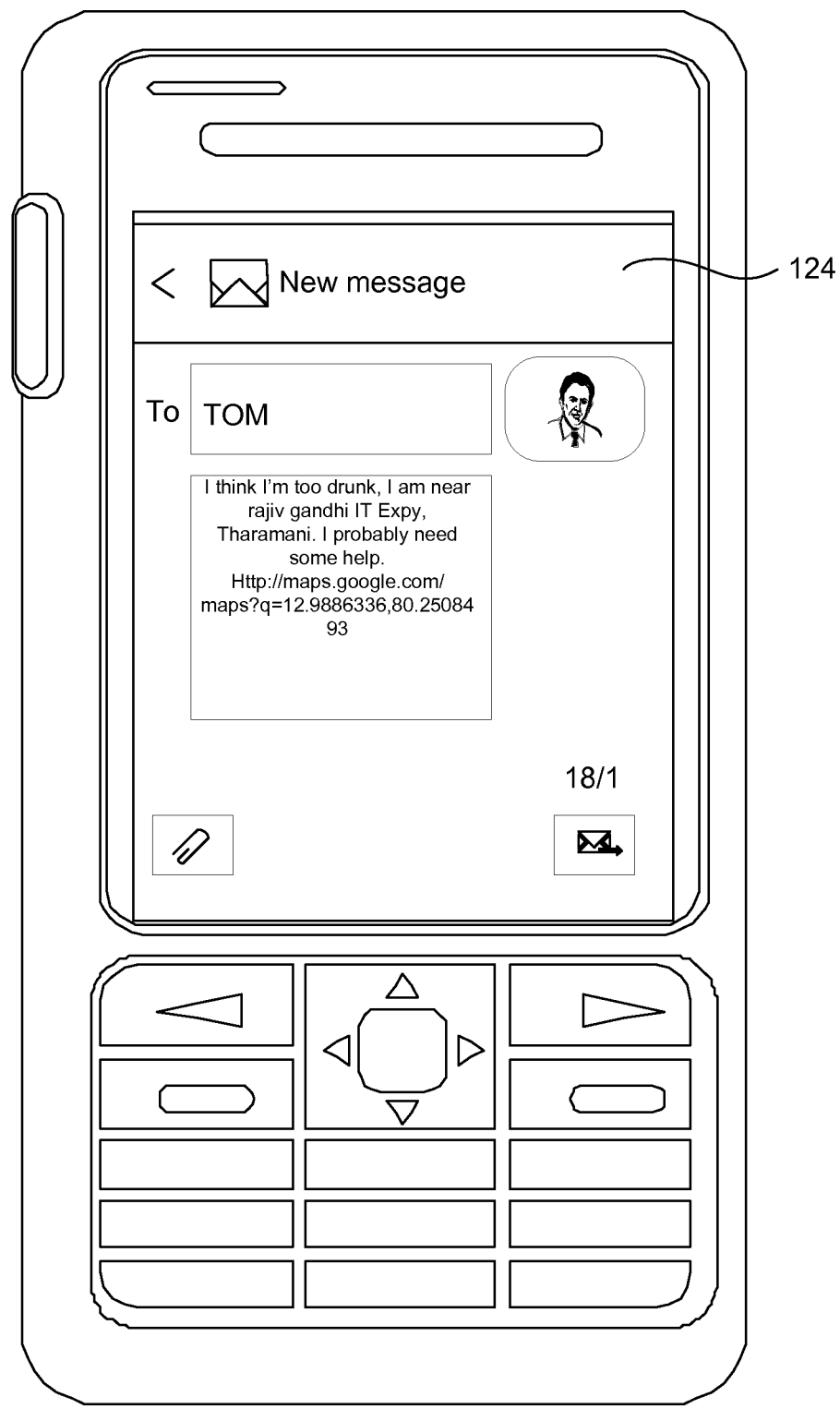
FIG. 12B illustrates a user interface view of a message that is generated and communicated to an emergency contact by the location based message generation module when the user exceeds at least one periodic threshold according to one embodiment of the present disclosure.
Figure 13:
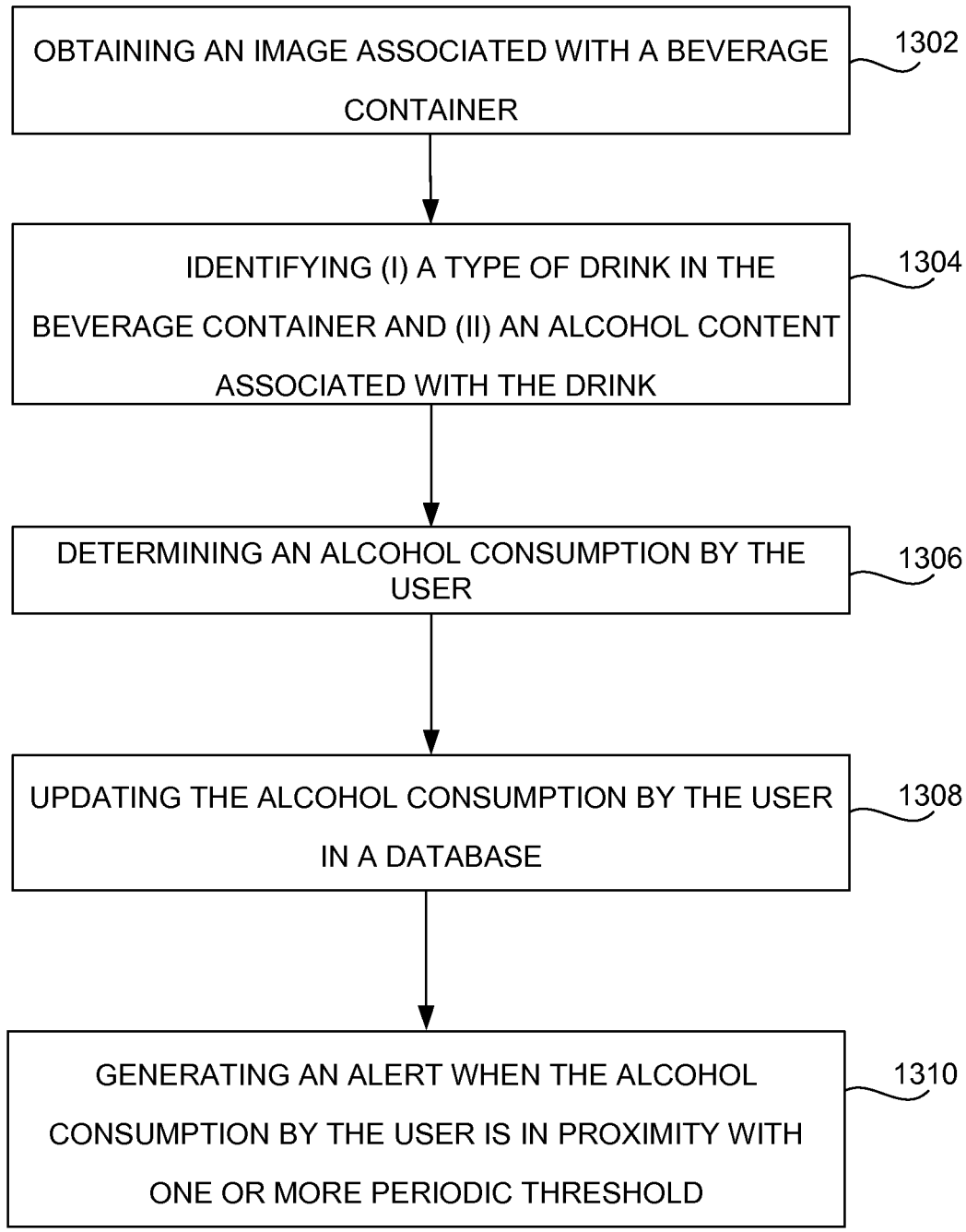
FIG. 13 is a flow diagram illustrating a method for managing alcohol consumption of a user according to an embodiment herein.

FIG. 12A illustrates a user interface view of a message that includes a map indicating a current location of a user, which is communicated to a communication device associated with a third party who provides a transportation support according to one embodiment of the present disclosure. The location based message generation module 222 obtains a current location of the user, and alerts the user to plan a transportation support when the user's BAC level is more than at least one periodic threshold. The location based message generation module 222 processes an input from the user indicating to avail a transportation support, and generates a message that indicates at least one (i) the current location of the user and (ii) an URL associated with a map or a map that indicates the current location of the user. The location based message generation module 222 communicates the message to a communication device associated with a third party who provides the transportation support.

With reference to FIGS. 1 through 12A, FIG. 12B illustrates a user interface view of a message that is generated and communicated to an emergency contact by the location based message generation module 222 of FIG. 2 when the user exceeds at least one periodic threshold according to one embodiment of the present disclosure. The message may include a current location of the user with a hyperlinked text to a map view for easy traceability. The user may add/remove one or more contacts at the time of sending the message.

With reference to FIGS. 1 through 12B, FIG. 13 is a flow diagram illustrating a method for managing alcohol consumption of a user of FIG. 1 according to an embodiment herein. In step 1302, an image associated with a beverage container is obtained. In step 1304, a type of drink in the beverage container is identified. Similarly an alcohol content associated with the drink is identified. In step 1306, alcohol consumption by the user is determined. In step 1308, the alcohol consumption by the user is updated in a database. The database may stores one or more periodic thresholds associated with alcohol consumption by the user. In step

1310, an alert is generated when the alcohol consumption by the user is in proximity with the at least one of periodic threshold.

Figure 14:
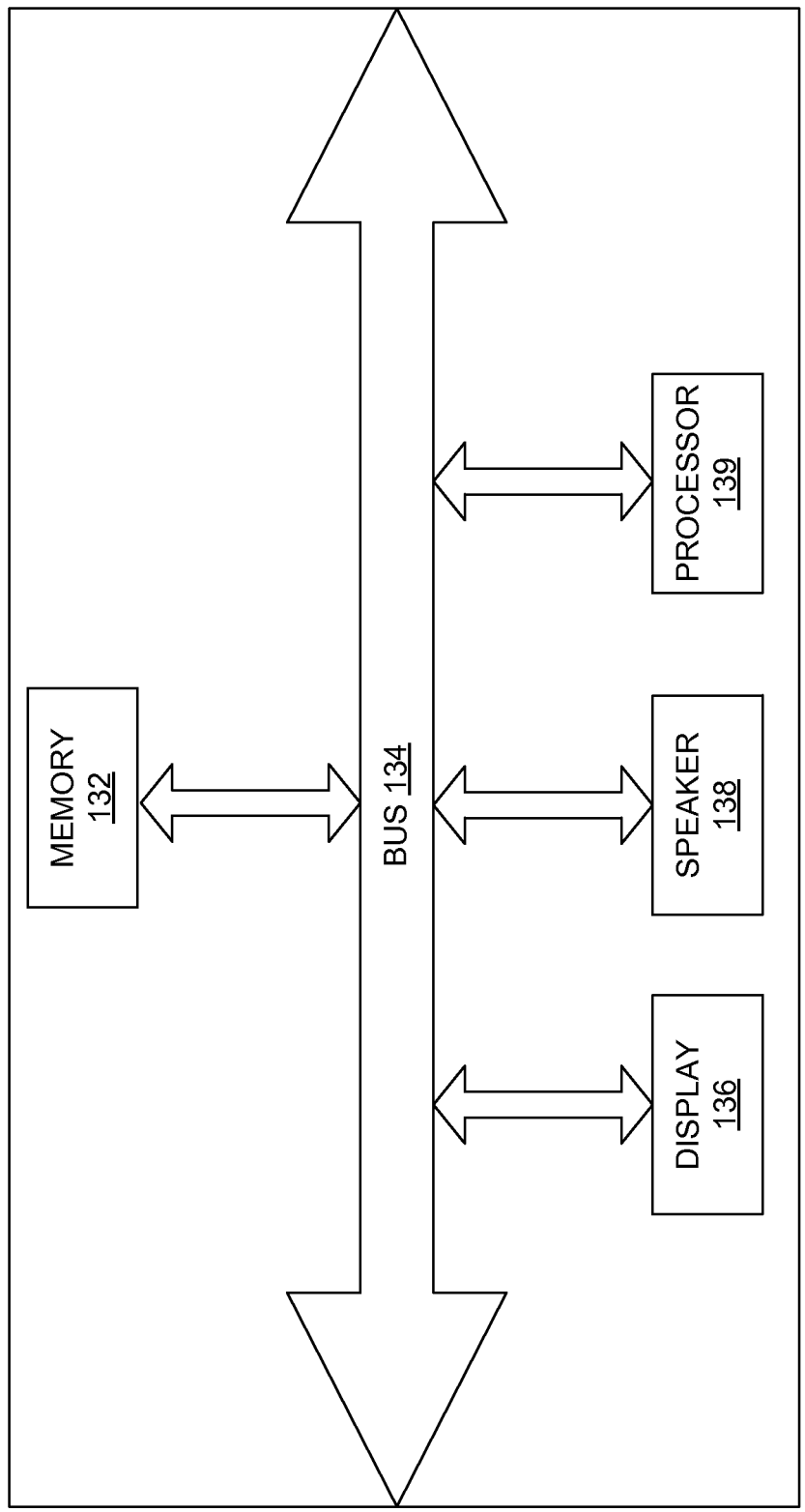
FIG. 14 is an exploded view of a mobile device of FIG. 1 in accordance with an embodiment herein.

FIG. 14 is an exploded view of a mobile device 104A-C of FIG. 1 in accordance with an embodiment herein. The mobile device 104A-C includes a memory 132 having a set of computer instructions, a bus 134, a display 136, a speaker 138, and a processor 139 capable of processing a set of instructions to perform any one or more of the methodologies herein, according to an embodiment herein. The processor 139 may also enable digital content to be consumed in the form of video for output via one or more displays 136 or audio for output via speaker and/or earphones 138. The processor 139 may also carry out the methods described herein and in accordance with the embodiments herein.

Digital content may also be stored in the memory 132 for future processing or consumption. The memory 132 may also store program specific information and/or service information (PSI/SI), including information about digital content (e.g., the detected information bits) available in the future or stored from the past. A user of the mobile device may view this stored information on display 136 and select an item of for viewing, listening, or other uses via input, which may take the form of keypad, scroll, or other input device(s) or combinations thereof. When digital content is selected, the processor 139 may pass information. The content and PSI/SI may be passed among functions within the mobile device using the bus 134.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly.

The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections).

In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can take the form of, an entirely hardware embodiment, an entirely software embodiment or an embodiment including both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, remote controls, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 15:
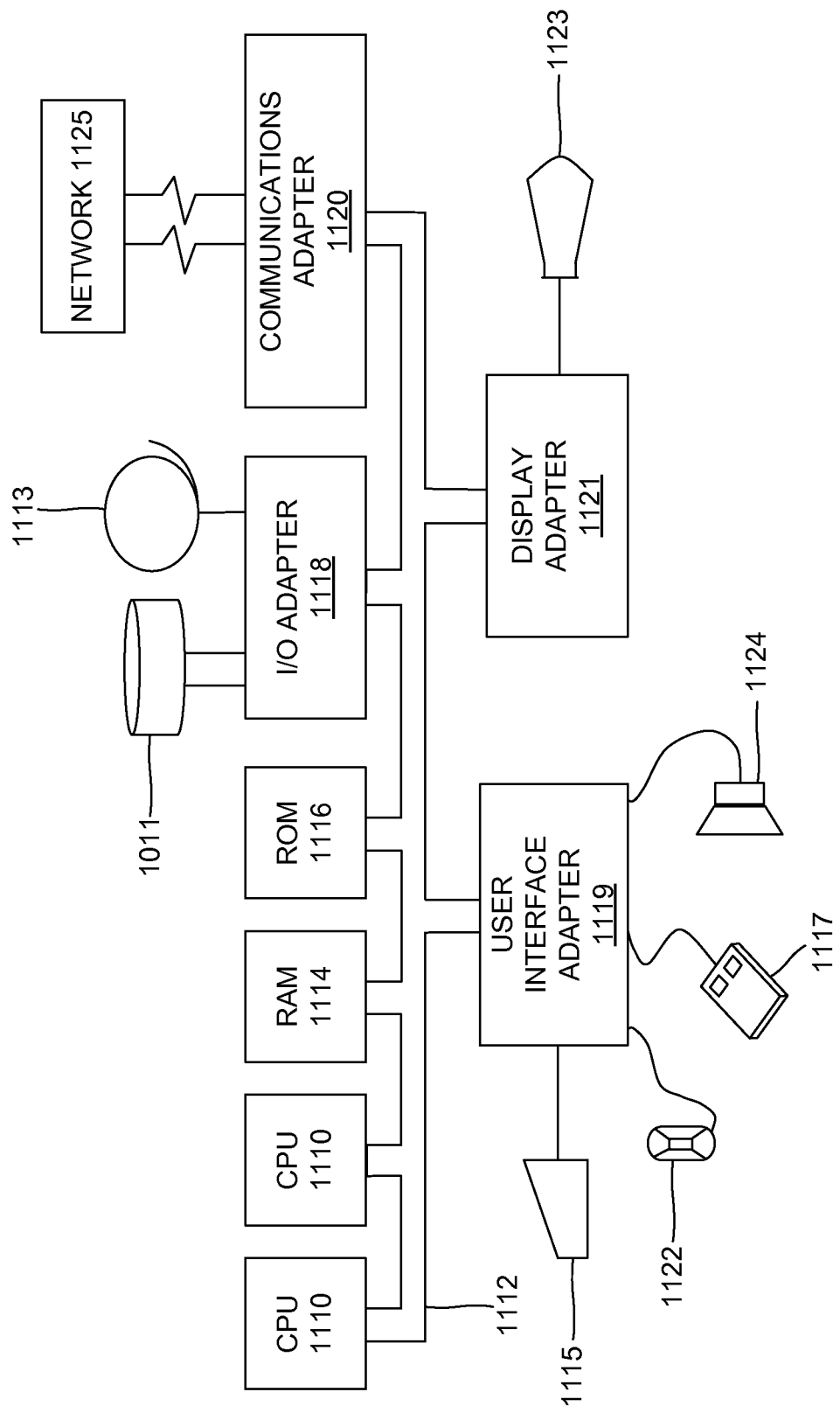
FIG. 15 is a schematic diagram of computer architecture in accordance with an embodiment herein.

A representative hardware environment for practicing the embodiments herein is depicted in FIG. 15. This schematic drawing illustrates a hardware configuration of an information handling/computer system in accordance with the embodiments herein. The system comprises at least one processor or central processing unit (CPU) 1110. The CPUs 1110 are interconnected via system bus 1112 to various devices such as a random access memory (RAM) 1114, read-only memory (ROM) 1116, and an input/output (I/O) adapter 1118. The I/O adapter 1118 can connect to peripheral devices, such as disk units 1011 and tape drives 1113, or other program storage devices that are readable by the system. The system can read the inventive instructions on the program storage devices and follow these instructions to execute the methodology of the embodiments herein.

The system further includes a user interface adapter 1119 that connects a keyboard 1115, mouse 1117, speaker 1124, microphone 1122, and/or other user interface devices such as a touch screen device (not shown) or a remote control to the bus 1112 to gather user input. Additionally, a communication adapter 1120 connects the bus 1112 to a data processing network 1125, and a display adapter 1121 connects the bus 1112 to a display device 1123 which may be embodied as an output device such as a monitor, printer, or transmitter, for example.

It will be appreciated that whilst it is advantageous to install the alcohol management platform application 302 on the platform 106 to reduce the amount of software installed on each mobile device 104A-C, the alcohol management platform application 302 may be installed on the mobile device if it has sufficient memory.

Thus by the use of the overall system including the individual disposable breathalyzer units, the alcohol management system application 114A-C on the mobile device 104A-C including the ability to easily obtain a record of the drinks consumed from images produced by the phone camera and the backup to each user provided by the platform 106, it is possible to produce cognitive feedback loops with the individuals and encourage the individuals towards lower alcohol consumption.

It will be appreciated that an alcohol management system in accordance with the invention may be readily individualized for the user. As the breathalyzer unit is convenient to use and disposable, a user can be encouraged to use such a system.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A device for managing alcohol consumption of a user, said device comprising:
   (i) a camera that captures an image associated with a beverage container;
   (ii) a display;
   (iii) a memory that stores (a) a set of modules, and (b) a database, wherein said database stores at least one periodic threshold associated with alcohol consumption by said user, wherein said periodic threshold is selected from at least one of (a) a daily threshold that indicates a maximum quantity of alcohol consumption in a day, (b) a weekly threshold that indicates a maximum quantity of alcohol consumption in a week; and (c) a monthly threshold that indicates a maximum quantity of alcohol consumption in a month; and
   (iv) a processor that executes said set of modules, wherein said set of modules comprise:
      (a) an alcohol content identification module, executed by said processor, that identifies a percentage of alcohol content associated with a drink in said beverage container based on (i) a shape associated with said beverage container, and (ii) a brand associated with said beverage container, wherein said alcohol content identification module identifies said shape and said brand of said beverage container based on edge detection technology applied on said image of said beverage container;
      (b) an alcohol consumption determination module, executed by said processor, that determines an alcohol consumption by said user based on information obtained from said image comprising (i) said shape associated with said beverage container, and (ii) said brand associated with said beverage container;
      (c) an alcohol consumption updating module, executed by said processor, that updates said alcohol consumption by said user in said database;
      (d) an alert generation module, executed by said processor, that generates an alert when said alcohol consumption by said user is in proximity with said at least one of (i) said daily threshold, (:ii) said weekly threshold, or (iii) said monthly threshold;
      (e) a location information obtaining module, executed by said processor, that obtains location information of said user;
      (f) a message generation module, executed by said processor, that generates a message that prompts said user to specify any alcohol consumed by said user during a time spent by said user at a preferred location for drinking, or in proximity to a location in which said user consumed alcohol in the past;
      (g) an electronic diary generation module, executed by said processor, that (i) obtains information related to (a) said alcohol consumption by said user which are determined based on said shape and said brand associated with said beverage container at various durations as a function of time, and (b) said alcohol consumed by said user during said time spent by said user at said preferred location for drinking, or in proximity to said location in which said user consumed alcohol in the past to generate an electronic diary, and (ii) maintains a visual record of said alcohol consumed by said user on said display; and
      (h) a location based message generation module, executed by said processor, that: (a) obtains said current location of said user from said location information obtaining module; (b) alerts said user to plan a transportation support when said user's blood alcohol content (BAC) level is more than at least one periodic threshold; (c) generates a location based message that comprises (i) said current location of said user, and (ii) an URL associated with a map or a map that indicates said current location of said user; and (d) communicates said location based message to a communication device associated with a third party who provides said transportation support.

2. The device of claim 1, wherein said alcohol content identification module identifies a type of drink in said beverage container, based on at least one of (a) said shape, and (b) said brand associated with said beverage container, wherein said alcohol consumption determination module further determines said alcohol consumption based on a drink level in said beverage container based on at least one of (a) said shape, and (b) said brand associated with said beverage container.

3. The device of claim 1, wherein said alcohol consumption determination module determines said alcohol consumption by said user based on a blood alcohol content (BAC) level of said user that is measured using a breathalyzer, wherein said electronic diary generation module obtains said blood alcohol content level of said user to generate said electronic diary.

4. The device of claim 1, wherein said set of modules further comprise: (a) a blood alcohol content (BAC) level record module, executed by said processor, that records a BAC level associated with said user when said user utilizes a breathalyzer for measuring said BAC level.

5. A method for managing alcohol consumption of a user, said method comprising:

(i) obtaining an image associated with a beverage container;
(ii) identifying a percentage of alcohol content associated with a drink in said beverage container based on (a) a shape associated with said beverage container, and (b) a brand associated with said beverage container, wherein said shape and said brand of said beverage container are identified based on edge detection technology applied on said image of said beverage container;
(iii) determining an alcohol consumption by said user based on (i) information obtained from said image comprising (a) said shape associated with said beverage container, and (b) said brand associated with said beverage container, and (ii) a blood alcohol content (BAC) level of said user that is measured using a breathalyzer;
(iv) updating said alcohol consumption by said user in a database, wherein said database stores at least one periodic threshold associated with said alcohol consumption by said user, wherein said periodic threshold is selected from at least one of (a) a daily threshold that indicates a maximum quantity of alcohol consumption in a day, (b) a weekly threshold that indicates a maximum quantity of alcohol consumption in a week; and (c) a monthly threshold that indicates a maximum quantity of alcohol consumption in a month;
(v) generating an alert when said alcohol consumption by said user is in proximity with said at least one of (i) said daily threshold, (ii) said weekly threshold, or (iii) said monthly threshold;
(vi) obtaining location information of said user based on a social medium update relating to said user's location;
(vii) generating a message that prompts said user to specify any alcohol consumed by said user during a time spent by said user at a preferred location for drinking, or in proximity to a location in which said user consumed alcohol in the past;
(viii) generating a location based message that comprises (a) said current location of said user, and (b) an URL associated with a map or a map that indicates said current location of said user;
(ix) communicating said location based message to a transportation support provider with said current location of said user when alcohol consumed by said user exceeds said at least one periodic threshold, wherein said location based message comprises said current location of said user with a hyperlinked text to a map view for easy traceability;
(x) obtaining information related to (i) said blood alcohol content (BAC) level associated with said user that is determined using said breathalyzer, (ii) said alcohol consumption by said user which are determined based on said shape and said brand associated with said beverage container at various durations as a function of time, and (iii) said alcohol consumed by said user during said time spent by said user at said preferred location for drinking, or in proximity to said location in which said user consumed alcohol in the past to generates an electronic diary; and
(xi) maintaining a visual record of alcohol consumed by said user on a display.

6. The method of claim 5, wherein (i) a type of drink in said beverage container and (ii) a drink level in said beverage container is identified based on at least one of (a) said shape, and (b) said brand associated with said beverage container.

7. The method of claim 5, further comprising: (a) recording said blood alcohol content (BAC) level associated with said user when said user utilizes said breathalyzer for measuring said BAC level.

8. The method of claim 5, further comprising: alerting said user to plan a transportation support when said user's blood alcohol content (BAC) level is more than said at least one periodic threshold.

9. A server for managing drinking habits of a plurality of users, said server comprising:
(i) a memory that stores (a) a set of modules, and (b) a database, wherein said database stores information associated with each of said plurality of users, and wherein said information comprises at least one of (a) a periodic threshold associated with alcohol consumption by each of said plurality of users, (b) a preferred duration of drink, (c) a preferred location to drink, and (d) a preferred person to drink with, wherein said periodic threshold is selected from at least one of (a) a daily threshold that indicates a maximum quantity of alcohol, consumption in a day; (b) a weekly threshold that indicates a maximum quantity of alcohol consumption in a week; and (c) a monthly threshold that indicates a maximum quantity of alcohol consumption in a month; and
(ii) a processor that execute said set of modules, wherein said set of modules comprise:
  (a) an alert generation module, executed by said processor, that obtains information associated with alcohol consumption by a user from a device that are determined based on (i) information obtained from an image of a beverage container comprising (a) a shape associated with said beverage container, and (b) a brand associated with said beverage container, and (ii) a blood alcohol content (BAC) level of said user that is measured using a breathalyzer, wherein said alert generation module processes said information associated with said alcohol consumption by said user to generate an alert when said alcohol consumption by said user is in proximity with said at least one periodic threshold; and
  (b) a message generation module, executed by said processor, that (i) obtains (a) a current duration associated with said alcohol consumption by said user, and (b) a current location of said user, and (ii) generates a message that prompts said user to check said blood alcohol content (BAC) level when:
    (i) said current duration exceeds said preferred duration of drinking;
    (ii) said user indicates said current location on a social medium along with said preferred person to drink; or
    (iii) said current location of said user is (a) in proximity to said preferred location for drinking, or (b) in proximity to a location in which said user consumed alcohol in the past; and
  (c) a multimedia content generation module, executed by said processor, that (i) obtains said information associated with said alcohol consumption by said user from said device, and (ii) processes said information associated with said alcohol consumption by said user to generate a multimedia content relating to (a) alcohol consumption or its harmful effects and (b) an image that indicates a look of said user in future when said user continues current alcohol consumption level, when said user exceeds said at least one of periodic threshold.

10. The server of claim 9, wherein said set of modules further comprise a reminder generation module that: (i) processes an input comprising a mood, a sleep or a tiredness pattern associated with (a) said blood alcohol content (BAC) level, or (b) consumption of a drink; and (ii) generates a reminder that comprises said mood, said sleep or said tiredness pattern when said user approaches said BAC level or selects said drink for consumption.

11. The server of claim 9, wherein said message generation module (i) generates said message at a random time that prompts said user to check BAC level, and (ii) generates an alert that is communicated to a caregiver when said user fails to check a BAC level.

* * * * *